United States Patent
Whalen et al.

(10) Patent No.: US 6,183,425 B1
(45) Date of Patent: Feb. 6, 2001

(54) METHOD AND APPARATUS FOR MONITORING OF DAILY ACTIVITY IN TERMS OF GROUND REACTION FORCES

(75) Inventors: Robert T. Whalen, Los Altos; Gregory A. Breit, Sunnyvale, both of CA (US)

(73) Assignee: The United States of America as represented by the Administrator of the National Aeronautics and Space Administration, Washington, DC (US)

(*) Notice: Under 35 U.S.C. 154(b), the term of this patent shall be extended for 0 days.

(21) Appl. No.: 08/540,614

(22) Filed: Oct. 13, 1995

(51) Int. Cl.$^7$ .................................................. A61B 5/103

(52) U.S. Cl. ............................................ 600/592; 600/595

(58) Field of Search ..................................... 128/774, 782, 128/779, 689

(56) References Cited

U.S. PATENT DOCUMENTS

| | | | |
|---|---|---|---|
| 4,367,752 | * 1/1983 | Yimenez et al. | 128/689 |
| 4,394,865 | 7/1983 | Sidorenko et al. | 128/782 |
| 4,409,992 | 10/1983 | Sidorenko et al. | 128/782 |
| 4,578,769 | 3/1986 | Frederick | 365/565 |
| 4,649,552 | 3/1987 | Yukawa | 377/24 |
| 4,703,445 | 10/1987 | Dassler | 364/561 |
| 4,771,394 | 9/1988 | Cavanagh | 364/561 |
| 4,774,679 | 9/1988 | Carlin | 364/550 |
| 4,855,942 | 8/1989 | Bianco | 364/561 |
| 4,956,628 | 9/1990 | Furlong | 340/323 |
| 5,033,013 | 7/1991 | Kato et al. | 364/561 |
| 5,052,130 | * 10/1991 | Barry et al. | 36/107 |
| 5,191,727 | * 3/1993 | Barry et al. | 36/107 |
| 5,373,651 | 12/1994 | Wood | 36/114 |
| 5,623,944 | * 4/1997 | Nashner | 128/779 |

OTHER PUBLICATIONS

Fuchs, et al. "Shortcuts in Cumulative Damage Analysis"(1977) 145–162 Fatigue Under Complex Loading: Advances in Engineering, vol. 6, SAE.

Winterstein, et al. "Load Models for Fatigue Reliability From Limited data" (1995) 73–82 *Proc. Wind Energy 1995, ASME, SED, 16.*

Carter, Et al. "Trabecular Bone Density and Loading History; Regulation of Connective Tissue Biology By Mehcanical Energy"; *J. Biomechanics*, vol. 20, No. 8, pp. 785–794 (1987).

(List continued on next page.)

*Primary Examiner*—Samuel G. Gilbert
*Assistant Examiner*—Pamela L. Wingood
(74) *Attorney, Agent, or Firm*—Robert M. Padilla; Gary G. Borda; John G. Mannix

(57) ABSTRACT

A device to record and analyze habitual daily activity in terms of the history of gait-related musculoskeletal loading is disclosed. The device consists of a pressure-sensing insole—placed into the shoe or embedded in a shoe sole—which detects contact of the foot with the ground. The sensor is coupled to a portable battery-powered digital data logger clipped to the shoe or worn around the ankle or waist. During the course of normal daily activity, the system maintains a record of time-of-occurrence of all non-spurious foot-down and lift-off events. Off line, these data are filtered and converted to a history of foot-ground contact times, from which measures of cumulative musculoskeletal loading, average walking- and running-specific gait speed, total time spent walking and running, total number of walking steps and running steps, and total gait-related energy expenditure are estimated from empirical regressions of various gait parameters to the contact time reciprocal. Data are available as cumulative values or as daily averages by menu selection. The data provided by this device are useful for assessment of musculoskeletal and cardiovascular health and risk factors associated with habitual patterns of daily activity.

2 Claims, 12 Drawing Sheets

OTHER PUBLICATIONS

Whalen, et.al. "A System for Monitoring and Recording Ground Reaction Forces During Daily Activity" *Advances in Bioengineering*, BED-26, pp. 535–538 (1993).

Robert Whalen; "Influence of Loading History on Muscle Fiber Cross–Sectional Area"; *American Society of Biomechanics 14th Annual Meeting*; (Nov. 14–16, 1990); Miami, Florida.

G.A. Breit et al; "Quantification of Cyclic Ground Reaction Force Histories During Daily Activity in Humans"; (Oct. 13, 1994);*American Society of Biomechanics Annual Meeting*.

R. Passmore et al; "Human Energy Expenditure"; *Physiol Review*; vol. 35, pp. 801–840, (1955).

Ridger Kram et al; "Energetics of Running: a new perspective"; *Nature*; vol.346, (Jul. 19, 1990).

R.T. Whalen et al; "Influence of Physical Activity on the Regulation of Bone Density";*J. Biomechanics*; vol. 21, No. 10, pp. 825–837, (1988).

Teresa M. Hutchinson et al; "Factors in daily physical activity related to calcaneal Mineral density in Men"; *Medicine and Science in Sports and Exercise*;(1995).

\* cited by examiner

METHOD AND APPARATUS FOR MONITORING OF DAILY ACTIVITY IN TERMS OF GROUND REACTION FORCES

FIELD OF THE INVENTION

This invention generally relates to the field of measuring physical activity and more specifically to an apparatus and method which monitors and quantifies habitual daily activity level in terms of the daily history of the vertical component of the ground reaction force.

BACKGROUND OF THE INVENTION

One's daily physical activity level is increasingly identified as an important contributor to and indicator of general health, risk of heart disease and musculoskeletal maintenance. For example, recent investigations indicate that declining activity level with age is a likely contributor to decreased muscle mass and strength, and decreased regional bone density in the elderly. However, measures of daily activity that may apply to the health and maintenance of the cardiovascular system may not apply to the musculoskeletal system. While the two are closely linked by the type and quantity of physical activity, cardiovascular fitness is assessed by metabolic measures whereas musculoskeletal fitness is quantified in terms of bone density and muscle strength and endurance.

The traditional approach to quantifying daily activity level has been to estimate the rate of daily energy expenditure in kilocalories per day from logbooks, pedometers, or activity monitors that record limb or trunk motion or accelerations. These methods provide some quantitative metabolic information about a subject's habitual activity level, but give no indication of the magnitude and frequency of musculoskeletal loading, particularly at relevant skeletal sites.

It is generally acknowledged and numerous studies concur that individuals engaged in activities generating high musculoskeletal forces have higher muscle mass and bone mass or density in regions subjected to the higher levels of force. Theoretical models and experimental evidence suggest that functions of the average daily history of peak cyclic tissue stresses and strains, when properly analyzed, will correlate to important functional measures of musculoskeletal fitness. While these models have not incorporated the effect of load-rate on bone or muscle adaptation explicitly, a number of experimental studies have indicated that load-rate may be an important factor contributing to an osteogenic stimulus. It has also been suggested that high load-rates accelerate the aging of cartilage tissue leading to osteoarthritis.

It is not possible to assess the contribution to musculoskeletal maintenance from daily activity including exercise without a method of monitoring and quantifying the significant external forces loading the body during normal daily activity. By virtue of force and moment equilibrium, high external ground reaction forces (GRFs) and ground reaction force-rates (GRF-rates or load-rates) are coincident with high lower limb internal muscle and bone forces, stresses/strains and stress-/strain-rates. Of the three components of the resultant ground reaction force, the vertical component, GRFz, is the most significant component loading the human body during normal daily activities. Studies have shown that the energy cost of walking is related to body weight and walking speed. Recent studies have also shown that the metabolic cost of locomotion is directly proportional to the magnitude of GRFz and duration of running.

It follows that a device that monitors, records and processes long term peak cyclic GRF and GRF-rate histories, and in particular, peak GRFzs and GRFz-rates, would be a unique and useful means of assessing normal daily activity in terms of metabolic and musculoskeletal variables. We have previously reported on a GRFz recording system that uses an analog capacitance insole sensor connected to an analog-to-digital converter and microcontroller worn at the waist (Whalen et al., 1993). This system has demonstrated the feasibility of collecting GRFzs, but is expensive, requires frequent calibration and replacement of the insole, and is not easily miniaturized.

A number of issued patents describe instrumented shoes or insoles for evaluation of exercise sessions. Yukawa (U.S. Pat. No. 4,649,552) describes a step counting device which is attached to an existing shoe, and measures distance traveled based on a fixed estimate of average stride length. Dassler (U.S. Pat. No. 4,703,445) describes a device which accounts for step-to-step gait variability during running by means of ultrasonic range finding between the left and right shoes.

Frederick (U.S. Pat. No. 4,578,769) and Cavanagh (U.S. Pat. No. 4,771.394), describe devices which track temporal characteristics of ground contact events to improve estimation of exercise-related parameters during running such as speed, distance traveled and energy (calories) expended. Similarly, Kato (U.S. Pat. No. 5,033,013) describes a device for determination, based on regressions to footfall frequency, of speed, distance traveled, and energy expenditure during walking. Each of these devices is designed to estimate work performed during either walking or running activity, but not both.

Devices based on step counting alone do not consider the magnitude of musculoskeletal loading, and alone cannot account for individual gait characteristics, gait speed and unpredictable high loading events that may influence bone and muscle significantly. For example, these devices cannot distinguish between slow and fast walking, both of which occur commonly during daily activity and differ significantly with respect to the magnitude of associated peak musculoskeletal forces. However, devices which consider the temporal characteristics of the footfall pattern may account for some of these variations.

Frederick (U.S. Pat. No. 4,578,769) observed an approximately linear relationship between running speed and foot-ground contact time, and subsequently describes a device which measures contact time to account for step-to-step gait variability to improve prediction of total distance from step count during running. Furlong (U.S. Pat. No. 4,956,628) describes a device which uses pressure sensors or contact transducers to detect the presence or absence of contact between both feet and the ground, but makes no interpretation of the duration or frequency of these events.

A number of devices have been disclosed which measure physical variables during human activity. Sidorenko et al. (U.S. Pat. No. 4,409,992) describe an electronic ergometer worn at the waist to measure the amount of performed work and magnitude of power developed by an individual during walking or running. Bianco (U.S. Pat. No. 4,855,942) describes a step counter worn on the wrist. However, activity monitors placed on the arm or waist are unreliable indicators of musculoskeletal loading. Another device described by Sidorenko et al. (U.S. Pat. No. 4,394,865) consists of an instrumented seismic mass connected to an alarm system for detection of abnormally high loads during exercise. This device is intended as an alarm system for overexertion, and is not designed as an ergometer. Carlin (U.S. Pat. No. 4,774,679) describes a device which can be attached to the ankle to measure and record local accelerations to estimate impact forces during athletic activity in humans and animals. Wood (U.S. Pat. No. 5,373,651) describes a device which estimates and stores force applied to an athletic shoe from a plurality of pressure sensors imbedded in the shoe sole.

None of the existing art describes devices to assess cumulative musculoskeletal loading during normal daily activity, which can consist of a combination of sedentary activity, walking, and running, in various proportions depending on the individual. None of the existing art can distinguish between and account for the differences between walking and running. The magnitude of the GRF, and consequently internal musculoskeletal loads, varies greatly with gait speed for both walking and running. Prior to the present invention, temporal parameters of gait have not been used to predict peak GRF. Although this can be tracked by direct measurement of the GRF, the temporal approach may be advantageous because temporal measurements can be made more easily, cheaply, and reliably than direct force measurements.

SUMMARY OF THE INVENTION

It is the object of the present invention to provide a method and device for quantifying normal daily activity in terms of the daily history of the vertical component of the ground reaction force, GRFz.

It is a further object of this invention to provide a means by which peak cyclic GRFzs are measured indirectly from analysis of foot-ground contact times, eliminating the need for an analog insole force sensor.

It is a further object of this invention to provide a means by which the peak horizontal (medial/lateral and anterior/posterior) components of the resultant ground reaction force (GRF) and the peak and average time derivatives of the ground reaction force in the vertical and anterior/posterior directions can be determined from analysis of foot-ground contact times.

It is a further object of this invention to provide a means by which the total number of walking steps, total number of running steps, total time spent walking, total time spent running, average walking speed, and average running speed during daily activity can be determined from a long term history of foot-ground contact times.

It is a further object of this invention to provide a means by which the history of foot-ground contact times and stride periods can be analyzed and presented in measures of daily metabolic energy expenditure.

It is a further object of this invention to provide a means by which the history of peak cyclic GRFzs can be analyzed and presented in terms of an Activity Index (AI) and Bone Density Index (BDI).

It is a further object of this invention to provide a means by which the Activity Index (AI) can be represented in terms of an "equivalent age" of the user.

It is a further object of this invention to provide a means by which the complete history of timing events, peak GRFzs, GRFz-rates, and other components, if desired, can be offloaded to a computer and analyzed in terms of statistical distributions.

These and other objects of the invention are accomplished with this inventive method and measurement device that uses foot-ground contact times: to characterize daily walking and running; to compute gait-related energy expenditure; and, to compute indices of daily physical activity related to skeletal loading. Specifically, estimated daily peak cyclic GRF and GRF-rate histories are computed from (1) ground contact time for walking cycles, (2) ground contact time or duty cycle (contact time divided by stride period) for running cycles and (3) special procedures for ground contact times falling outside the contact-time interval encompassing walking and running. The vertical component, GRFz, is the most relevant and is discussed in greatest detail here. All other GRF or GRF-rate components are computed in the same way, but are only available from offline analysis of the data.

The device consists of a sensor placed in the shoe which detects contact of the foot with the ground. The sensor is coupled to a battery-powered waist-worn, ankle-worn, or shoe clip-on digital data logging system with real-time clock and microprocessor interfaced to random access memory, user pushbuttons, and an alphanumeric display. During normal use, the time of occurrence of each "significant" foot-down and foot-up event is recorded. Signal processing methods are employed to avoid confusing most noise and spurious non-significant contacts, e.g., foot tapping, as true gait cycles. In the preferred embodiment, a pressure sensor, connected to a gas-filled insole, outputs a signal that is thresholded to capture primarily weight- bearing contact.

On user command, following request for "cumulative" or "average daily" data analysis, a program is initiated that first filters the sequence of stored timing events by removing contact times, in pairs of foot-down and foot-up events, that are not likely to be gait-related loading cycles. Specifically, the program first discards very slow and very fast ground contact times known to lie outside the range of gait that includes walking, running and "special events" such as stair climbing. Next, in sequence, the algorithm 1) identifies a ground contact time as either walking, "special events", or running by the value of the contact-time interval and 2) rejects any contact pair that falls outside of the known walking or running contact time to stride period relationship. Note that for the purpose of this embodiment, ground contact times that fall between walking and running are classified as "special events" and will be treated as walking cycles.

The remaining timing events are then analyzed as consecutive walking or running gait cycles having a foot-ground contact time, $t_c$, and stride period, T. Cumulative sums of the reciprocal of the foot-ground contact time ($1/t_c$) and stride periods (T) are kept separately for both walking and running. In addition, a cumulative sum of stride periods normalized by respective ground contact times ($T/t_c$) is kept for computation of gait variables and energy expenditure. The timing events are also converted to peak cyclic GRFzs using appropriate walking and running regression equations. "Special events" are currently treated as walking cycles, although they extrapolate to higher GRFz values than walking. Note that ground contact times identified as running are first normalized by stride period (duty cycle) prior to converting to peak GRFz loading cycles.

Further processing yields cumulative and average daily: walking and running mean speed, steps, and duration; total gait-related energy expenditure; Activity Index; Bond Density Index; and an "equivalent age" of the user in terms of level of skeletal loading. The history of the GRFz, load-rates and other GRF components can be further analyzed by offloading to a computer. The importance of summarizing in terms of Weibull distributions (Winterstein et al., 1995) is that it may be possible to relate specific indices of fitness or health risk to distribution parameters or through application of our mathematical model of tissue functional adaptation (Carter et al., 1987; Whalen et al., 1988).

DESCRIPTION OF THE PREFERRED EMBODIMENT

Theory

A. Musculoskeletal Adaptation to Physical Activity

Figure 1:
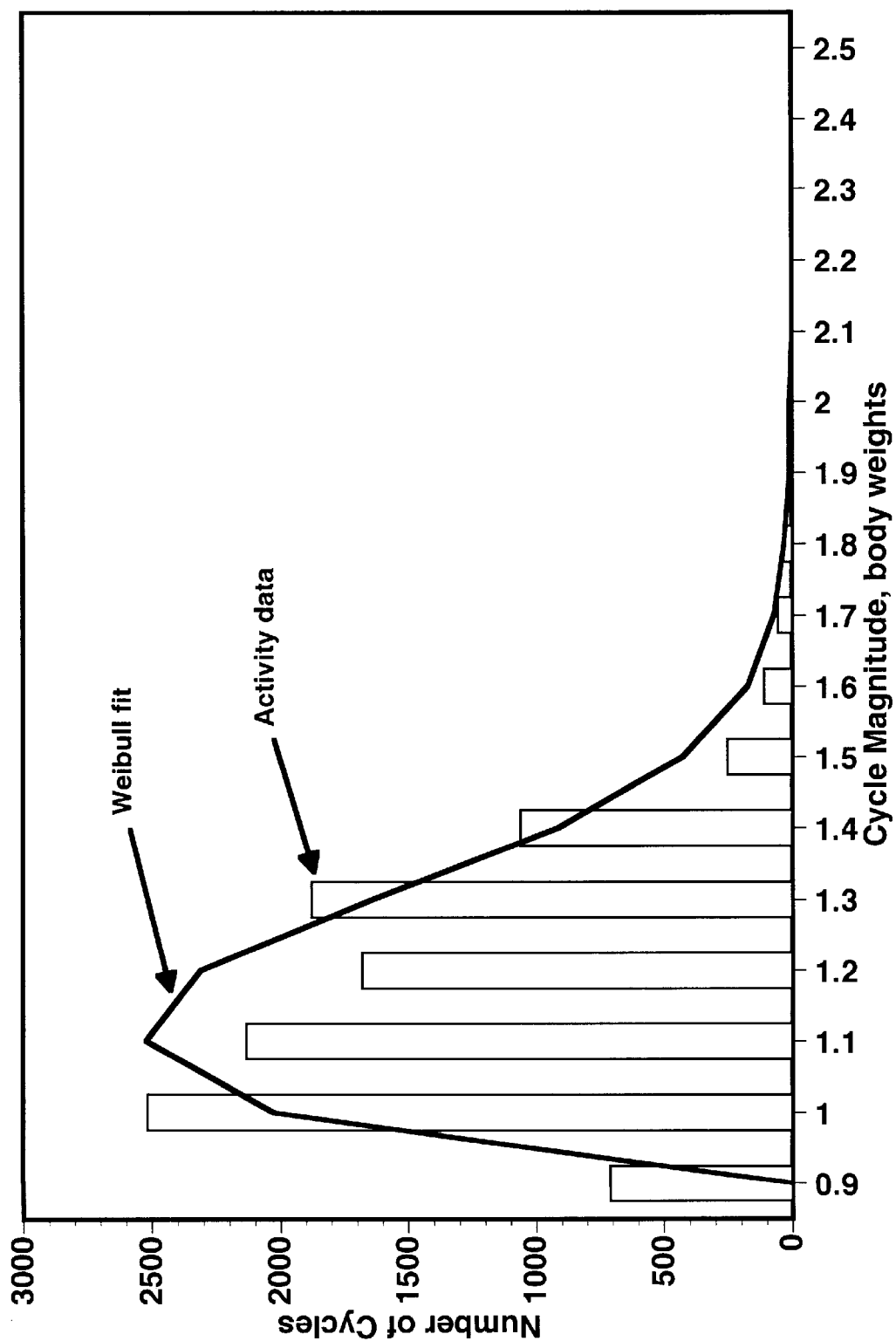
FIG. 1 is a histogram and best Weibull distribution fit of cyclic peak vertical ground reaction forces (GRFZ) collected during 40 hours of normal daily activity.

It has been postulated (Carter et al., 1987; Whalen et al., 1988; Whalen, 1990) that musculoskeletal tissues are regulated in order to maintain a constant level of average daily tissue loading stimulus, $\Omega_t$, $$\psi_t = K[\sum \sigma_{ti}^\alpha]^{\frac{1}{\alpha}} \tag{1}$$

where K is a tissue-specific constant, $\sigma_{ti}$ is the peak tissue level effective stress for each ith daily loading cycle. A tissue-specific weighting factor, $\alpha$, determines the relative importance of the effective stress magnitude compared to the number of loading cycles. In this model the daily tissue stimulus is the sum contribution from all daily loading cycles.

In the case of bone, if activity level increases such that $\Psi_t$ increases, then a compensatory increase in bone density, or an increase in bone cross-section in the case of a long bone, will take place to return the stimulus to its equilibrium position. Increased bone density or increased bone cross-sectional size act to reduce local bone tissue stress. Conversely, if $\Psi_t$ is reduced by a decline in activity, then bone mass will be lost until tissue stresses are sufficiently high to again return $\Psi_t$ to its equilibrium position. Muscle fiber cross-sectional area is regulated in the same way.

Expressions for bone density and fiber cross-sectional area can be derived by relating bone and muscle tissue effective stresses to their respective continuum effective stresses with the following results:

$$\rho = K_b[\sum \sigma_{ci}^m]^{\frac{1}{2m}} \text{ and } a_x = K_m[\sum f_i^k]^{\frac{1}{k}} \tag{2, 3}$$

where $\sigma_{ci}$ is the peak continuum cyclic effective stress in bone, and $f_i$ is the peak cyclic fiber force. The exponent m for bone is estimated to be between 4 and 8. The value of m may be bi-linear with a lower value for low load cycles and a higher value for high load cycles. Values for k have not been estimated from literature data, but high values (k>8) are consistent with high force, low cycle (resistance) exercise increasing fiber cross-sectional area more effectively than low force (aerobic), high cycle exercise.

Normal daily activities such as standing, walking, and running impose two external forces on the body: body weight (constant) and the ground reaction force (GRF) composed of body weight (BW) and the inertia force accelerating and decelerating the center of mass of the body during activity. High GRFs produce large internal muscle and bone forces. Mechanical strains on the surface of animal leg bones, monitored with strain gages, indicate that for a wide range of gait speeds and modes of locomotion surface strain patterns are similar and follow the magnitude of the GRF. These results suggest that the musculoskeletal forces in lower limbs are approximately scaled by the magnitude of the GRF during activities of the same type.

The GRF has three orthogonal components: a vertical component that supports body weight and accelerates or decelerates the body in the direction of gravity; an anterior/posterior force component that accelerates and decelerates the body in the direction of motion; and a medial/lateral force component of low magnitude that controls side sway. The vertical component, GRFz, is the most significant force loading the body during stance phase when internal muscle and bone forces are the greatest. Therefore, if lower limb musculoskeletal loading and tissue stresses are proportional to GRFz, then it follows from equations (1) and (2) that the daily bone loading stimulus and lower limb bone density, loaded primarily by ground reaction forces, are approximately proportional to $$\psi_t \propto \beta[\sum (GRFz_i)^m]^{\frac{1}{m}} \text{ and } \rho \propto \beta^{\frac{1}{2}}[\sum (GRFz_i)^m]^{\frac{1}{2m}}. \tag{4, 5}$$

In these expressions it is understood that the peak value of the vertical component (GRFZ) is in units of body weight (BW). For example, if an individual were standing on one foot, GRFz would be equal to one body weight (1.0 BW). Peak cyclic values of GRFz range from approximately 1.0–1.5 BW during walking and 2.0–3.0 BW during running, depending on gait speed and individual variations in gait mechanics. Also, $\beta$ is equal to the subject's body weight normalized to a standard recommended body weight based on subject height.

It follows that monitoring daily peak vertical forces, GRFz, may give a good approximation to lower body musculoskeletal loading and general physical activity. It is noted that muscle have and bone may have different tissue stimulus values for the same GRFz history since exponents m and k may be different. This preferred embodiment quantifies the musculoskeletal loading stimulus in terms of a bone stimulus. In particular, we can define two new variables, an Activity Index, AI, and a Bone Density Index, BDI, from equations (4) and (5) above that provide the user with useful activity level and bone density information:

$$\frac{\psi_t}{\beta} \propto AI \equiv \left[\sum (GRFz_i)^m\right]^{\frac{1}{m}} \text{ and} \quad (6,7)$$

$$\rho \propto BDI \equiv \beta^{\frac{1}{2}}\left[\sum (GRFz_i)^m\right]^{\frac{1}{2m}}.$$

For each user, $\beta$ is determined from the user's height and a stored table. The Activity Index reflects a user's true activity level since it is unbiased by body weight. However, the absolute value of bone density is affected by body weight. Thus, heavy people could have relatively high bone density even though they may be sedentary. To account for both activity level and bone density, we have two indices. Equation (6) provides a way of relating daily GRFz loading histories to a daily loading stimulus as a method of quantifying daily activity level. Equation (7) provides a way of relating daily GRFz loading histories to lower limb bone density, particularly in the calcaneus (heel). This is important since the heel is known to be response to changes with age and activity level (Hutchinson et al., 1995).

B. Application of Statistical Distributions to Daily GRFz Histories

The value of the Activity Index, A1, and Bone Density Index, BDI, give the best single quantitative measures of daily activity for the assessment of musculoskeletal fitness. A number of combinations of daily high and low load cycles may produce similar values of AI and BDI. For example, because the exponent m is thought to be between 4 and 8, a small number of high load cycles may have the same AI and BDI values as a large number of low load cycles. Clearly, the pattern of activity producing these two different load distributions will be different.

To gain a better description of individual daily activity, the complete histogram of peak GRFz loading cycle magnitudes can be summarized in terms of the Weibull probability distribution, which is known to be appropriate for modeling the distribution of peaks of a random loading history (Winterstein et al., 1995). Distributions of this type are asymmetric, and possess a long tail toward the highest values of the distribution. In the case of human cyclic GRFz histories, the area under the distribution is an index of the total amount of activity (i.e. total number of cycles) and the width of the tail is an indicator of the intensity of activity. A sample fit to 40 hours of normal activity is shown in FIG. 1.

Accurate characterization of the distribution tail (highest-magnitude cycles) is crucial because 1) theoretical models and experimental evidence indicate that the high-magnitude loading cycles provide a disproportionately high contribution to bone tissue loading stimulus and density (m between 4 and 8 in equations 4 and 5); and 2) the presence of activity at these extreme values varies greatly among individuals and is a good indicator of overall intensity of daily activity. We also postulate that width and area under the distribution decline with age, as individuals become less active and less intense in their activity, resulting in fewer daily loading cycles of lesser magnitude. For example, it is known that preferred walking speed declines with age, resulting in lower peak forces and a consequently narrower loading distribution.

Experiments

A. Laboratory Measurement of GRF and Ground Contact Time

Twenty-four male subjects walked and ran across a force plate to test the accuracy of using ground contact time or ground contact time normalized by stride period to estimate both vertical and horizontal force (load) and force-rate (load-rate) components of the ground reaction force. Three walking and three running speeds were selected to cover the range of slow to fast walking and running.

Results

Figure 2A:
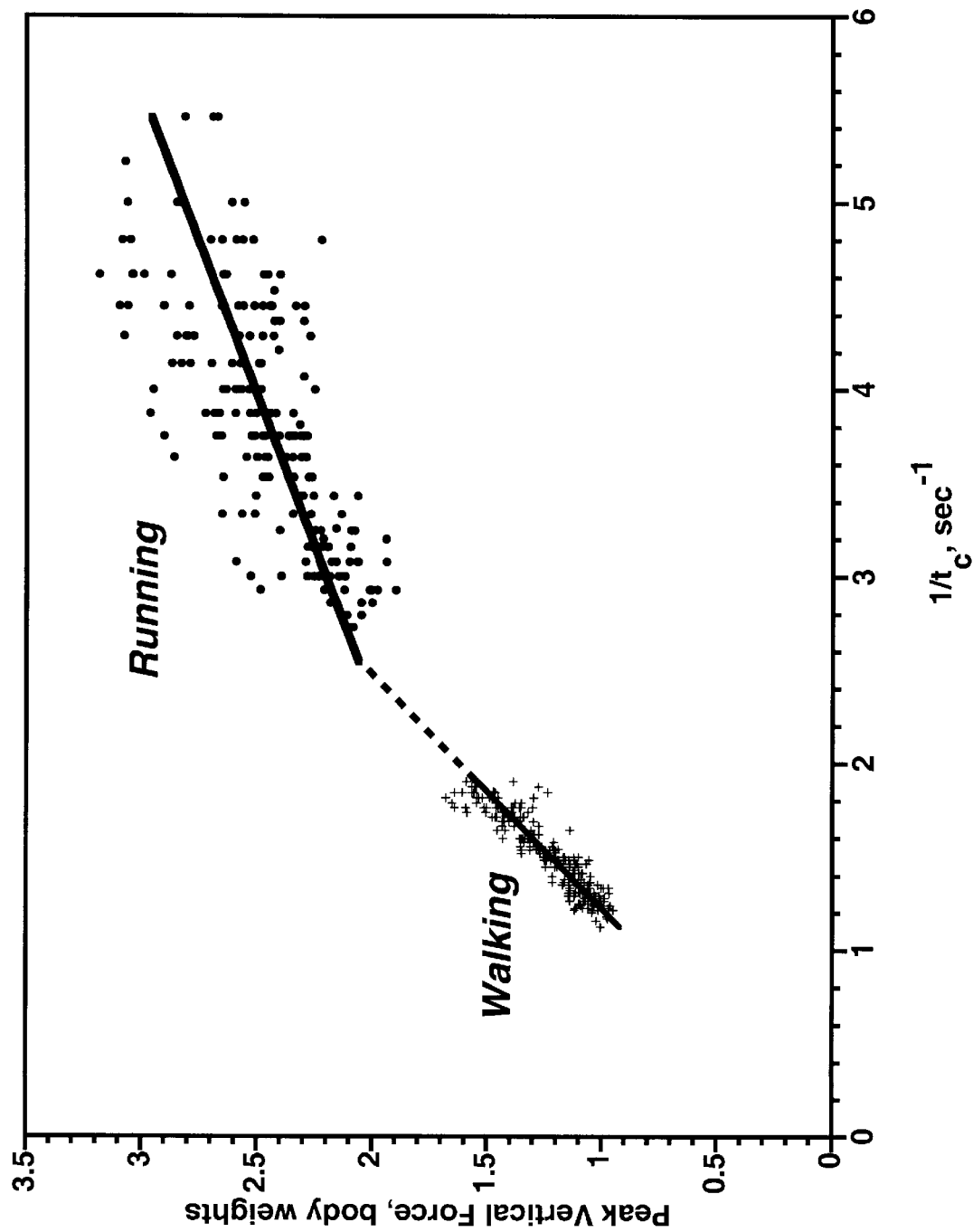
FIG. 2a is a graph showing the relationship between the reciprocal of the ground contact time ($1/t_c$) and peak cyclic GRFz during walking and running.
Figure 2B:
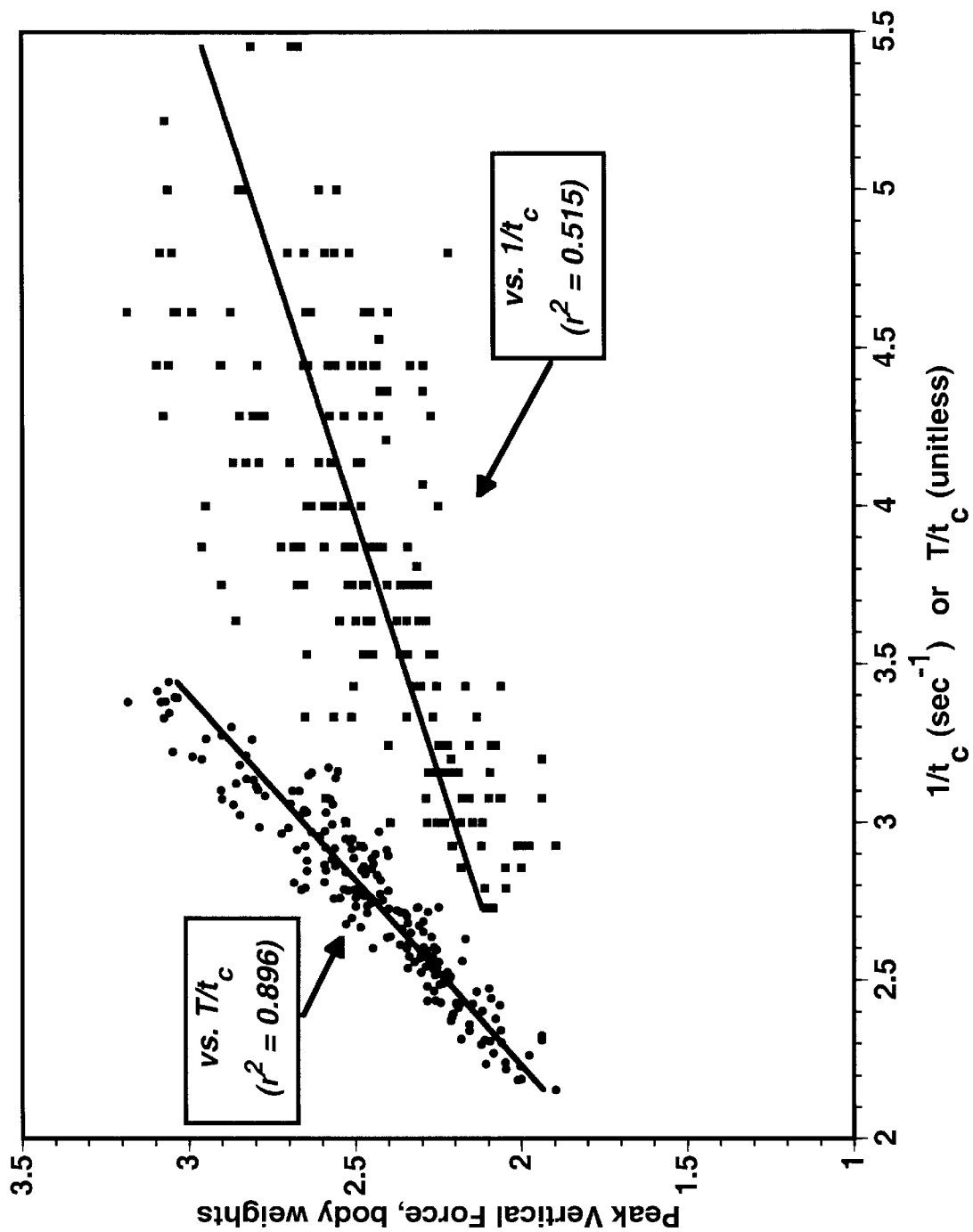
FIG. 2b is a graph showing the improved correlation between the reciprocal of the ground contact time, normalized by stride period, and peak cyclic GRFz during running.

The laboratory data indicate that walking and running possess disparate ranges of typical contact times ($t_c$), each contact event can be identified as one of these two types of gait, and a separate regression equation used on this basis. An inverse relationship was found between ground contact time and GRFz as depicted in FIG. 2a. FIG. 2b illustrates the improvement in GRFz prediction during running when ground contact time is normalized by stride period.

If a cycle is identified as walking (0.5 s<$t_c$<0.9 s), a suitable regression equation is:

$$\text{Peak GRFz (body weights)} = 0.795 \ (1/t_c) + 0.029. \quad (8)$$

If a cycle is identified as running (0.15 s<$t_c$<0.37 s), a suitable regression equation is:

$$\text{Peak GRFz (body weights)} = 0.307 \ (1/t_c) + 1.282. \quad (9)$$

Increased accuracy is achieved if the regression relationship for running is normalized by stride period computed from successive foot-down contacts $$\text{Peak GRFz (body weights)} = 0.856 \ (T/t_c) + 0.089. \quad (10)$$

Similar relationships were found for the two horizontal force components and loading rates in the three component directions. Accuracy was found to be highest between contact times and the vertical force component, GRFz. GRFz was predicted from contact time alone within ±8% (±1 SD) for both walking and running. When running ground contact time was normalized by stride period, accuracy improved to ±4%.

B. Outdoor Measurement of Normal Walking and Running

A second study was performed outside the laboratory to test the ability of the method 1) to distinguish normal walking and running from ground contact time, and 2) to predict peak cyclic GRFz from regression equations (8) and (10) in a setting approximating normal daily activity.

One subject was outfitted with an analog insole force sensor and portable data logger, developed in our laboratory, that was programmed to store foot-ground contact times and peak cyclic GRFzs. The subject walked and ran outside at different self-selected speeds for a period of 40 minutes.

Results

Walking and running cycles were detected separately without significant error from ground contact time intervals empirically determined in Experiment A. Regression equations listed above were used to convert foot-ground contact times to GRFzs. GRFzs from contact times were compared to peak GRFzs measured with the insole force sensor.

Figure 3:
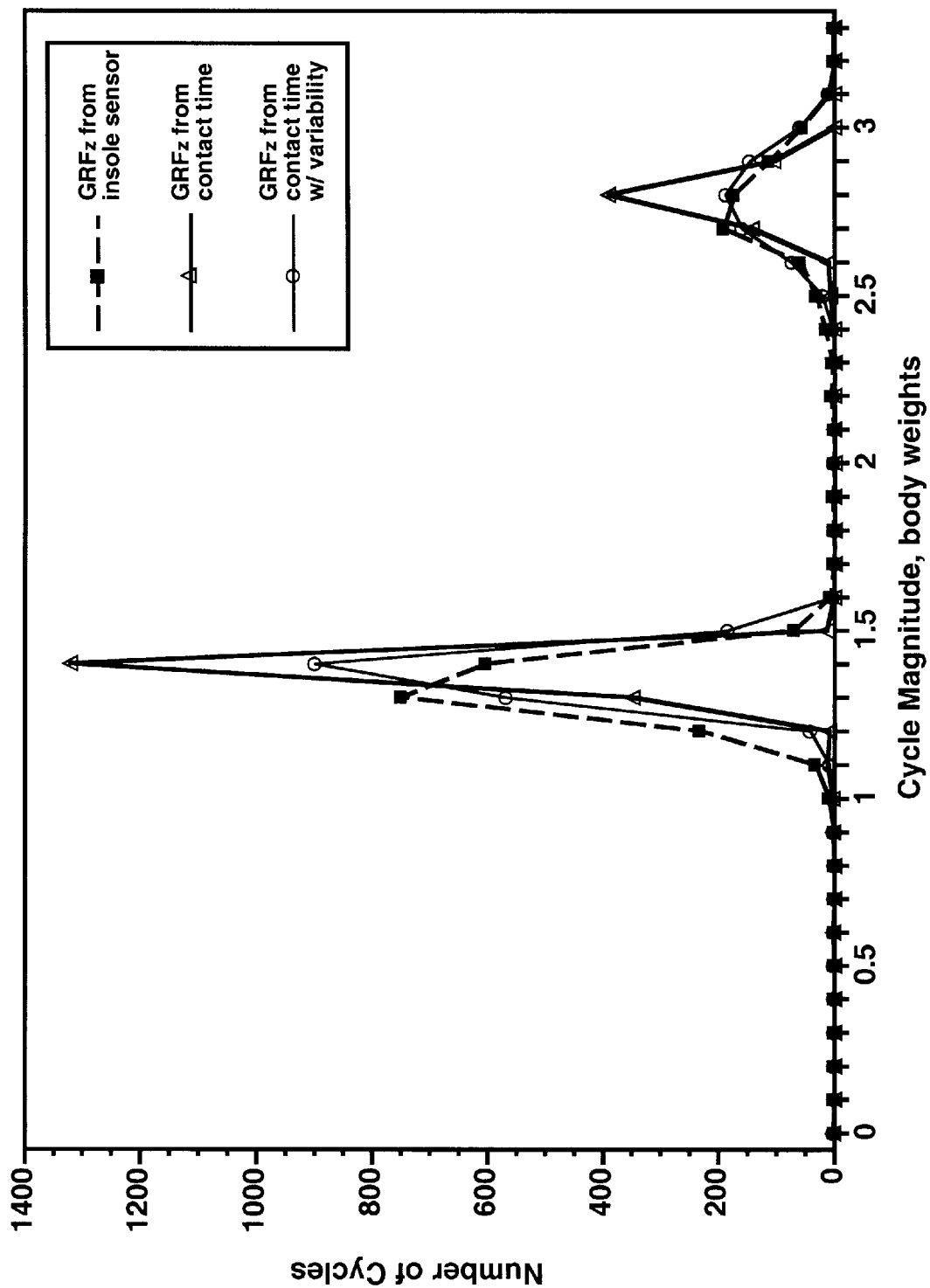
FIG. 3 compares measured GRFz loading histories with GRFzs computed from ground contact times and ground contact times with variability. Data collected outside during 40 minutes of walking and running.

GRFzs computed from regression equations (8, 9, or 10) imply perfect correlation between contact time and GRFz. In reality GRFzs are randomly distributed about the regression line with a certain variance, $s^2_{xy}$. To simulate the variability in these forces, a Gaussian random number of variance $s^2_{xy}$ was added to each GRFz estimated from the appropriate regression equation. The results are shown in FIG. 3. Both contact time and contact time with variability estimated accurately the mean loading range of walking and running; contact time with variability also detected the spread of the distribution.

Discussion

A. Basic User Operation

At the start of operation, the user enters his or her gender, body weight, height and age. These are used internally for referencing the user to the general population. Once the data has been input, it will remain unless the user wishes to reset the values by scrolling through a menu displayed on the alphanumeric display 80. The user then inserts the insole 10 into his/her shoe 50 and initiates data collection by pushing the Start/Pause button 90.

Contact time events will now be collected until the Start/Pause button 90 is pushed. Unless the Clear/Reset mode is selected from the menu, pushing the Start/Pause button 90 again will restart the collection process without loss of data. The Timer 170, however, is not halted and keeps a continuous time record. At any time the user may wish to look at cumulative data. He or she does so by pausing the device with button 90, then he or she scrolls through the menu to select Cumulative Analysis (see FIG. 11). To examine average daily values, the user again pauses the device with button 90, scrolls through the menu and selects Daily Average Analysis (see FIG. 11 for complete description). The quantities communicated to the user are listed in FIG. 11.

B. System Description

Figure 6:
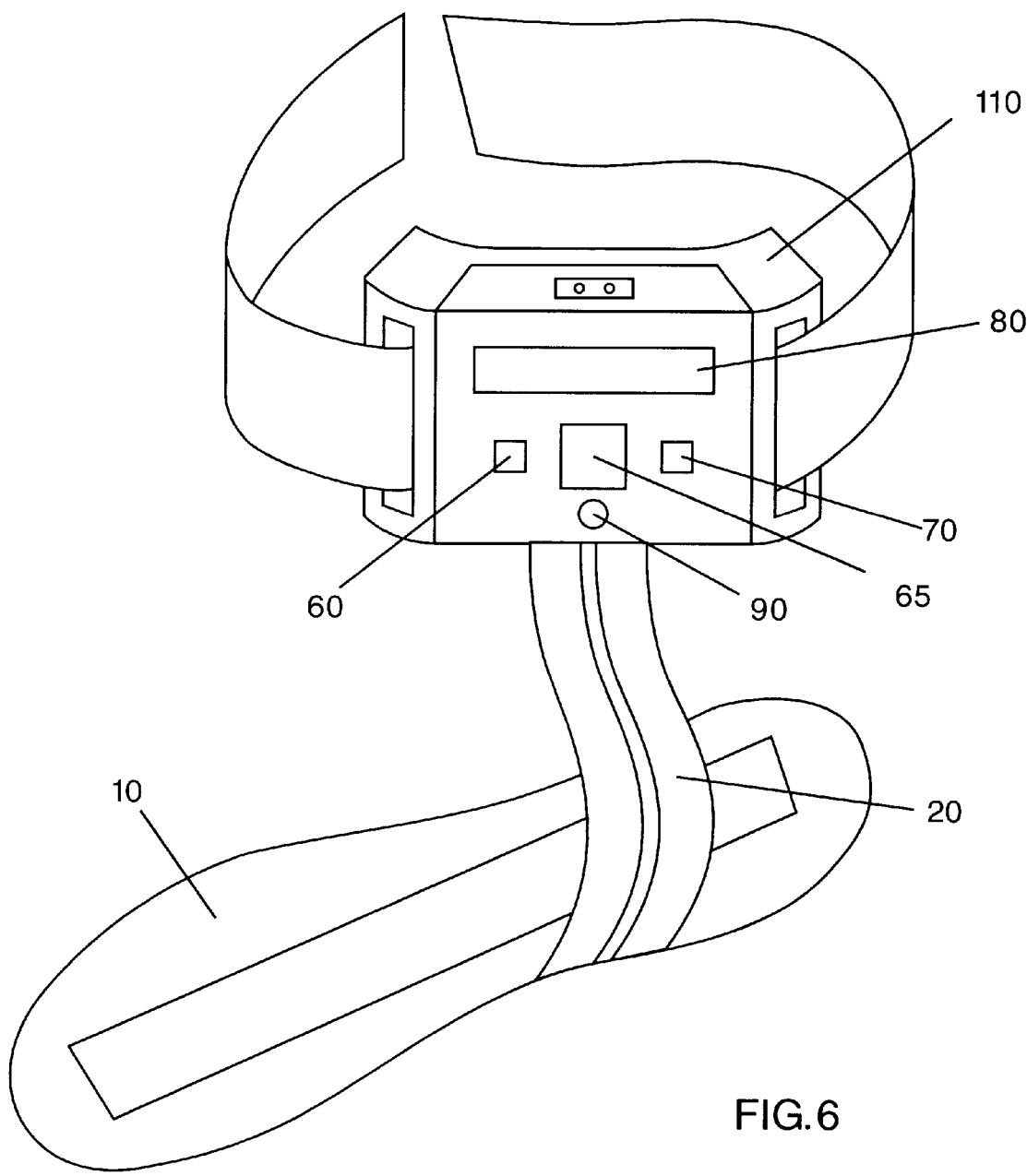
FIG. 6 is a perspective view of the principal components of the invention: the contact insole, and data processing/logging unit.
Figure 7:
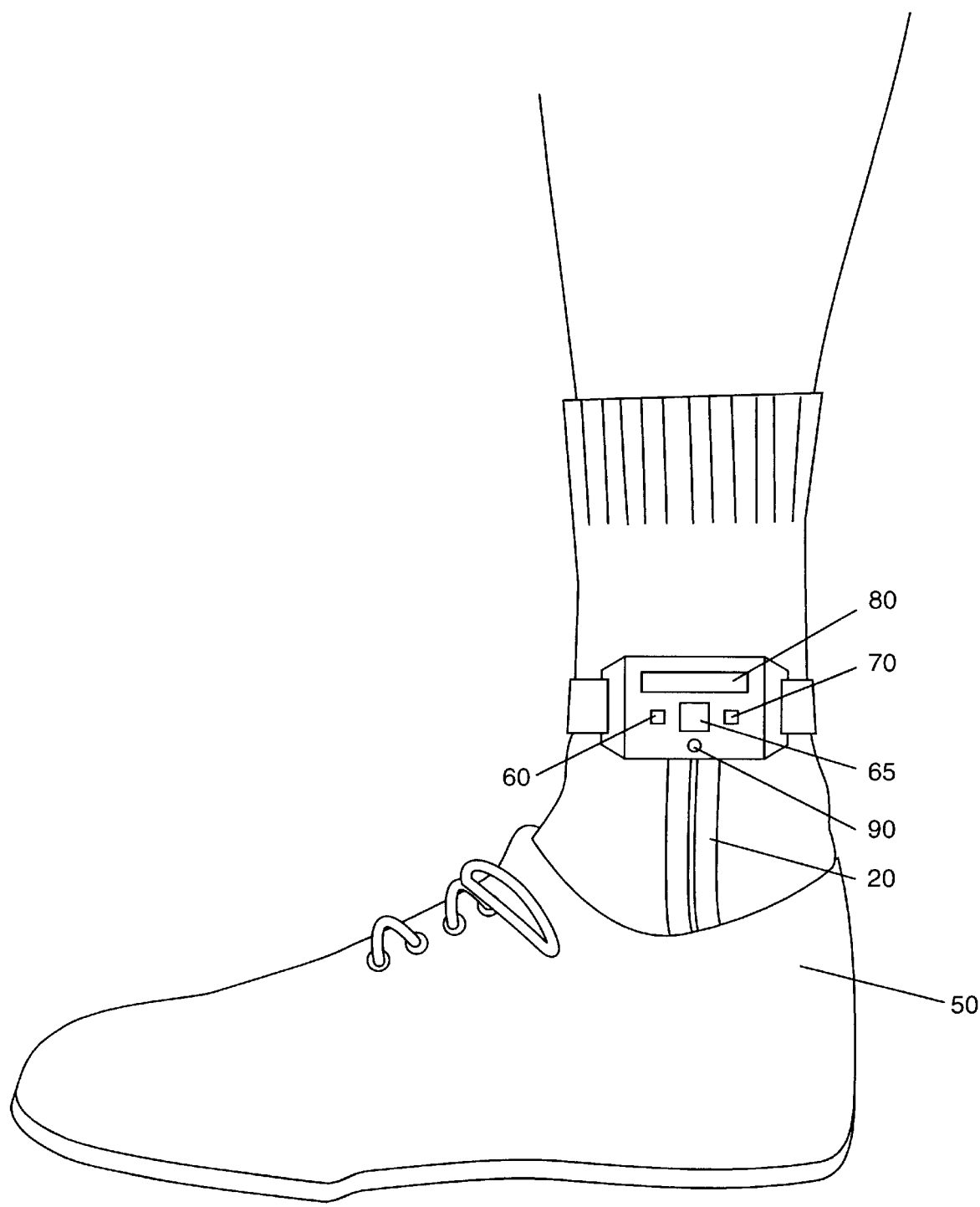
FIG. 7 is a perspective view of the system during normal use, with the data processing/logging unit worn on the ankle of the user.

The system consists of two principal components (see FIGS. 6 and 7): a gas-filled insole 10, insertable into the user's shoe 50, for detection of foot-ground contact; and an electronic data processing/logging unit 40 attached to the user's ankle by strap 30. The two components are connected by pressure tubing 20.

Figure 8A:
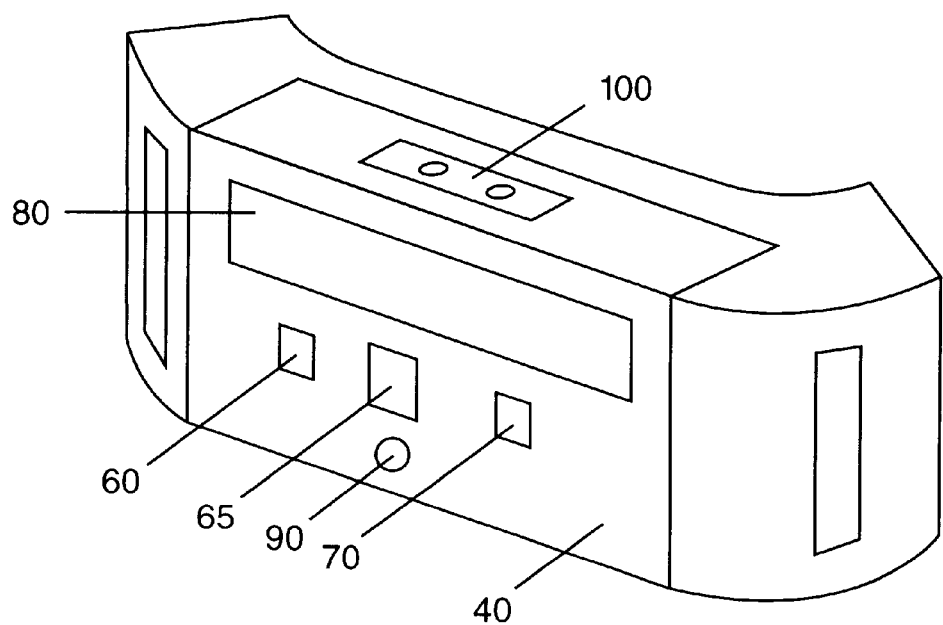
FIG. 8a and FIG. 8b are perspective views detailing the external features of the data processing/logging unit.
Figure 8B:
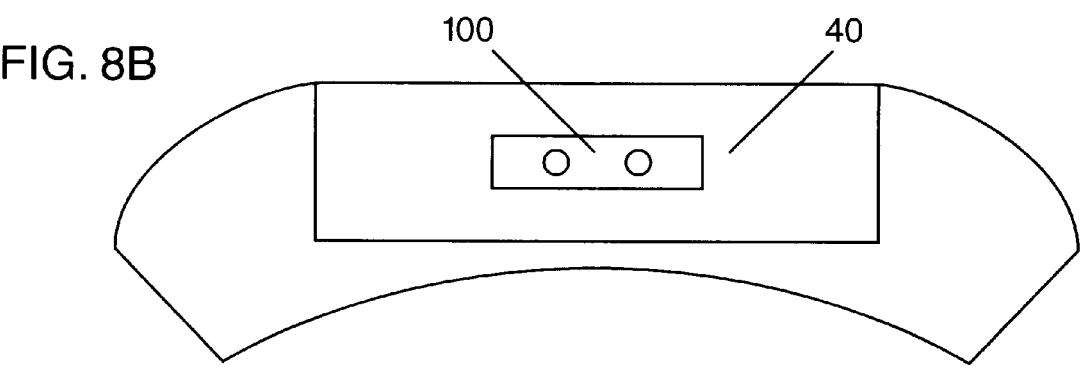

FIGS. 8a and 8b provide a close-up external view of the data processing/logging unit. All elements of the unit are contained in rigid housing 40, which is attached to a flexible, formable backing 110, for comfortable positioning against the ankle of the user. A digital data port 100 is provided for offloading of stored data to an external microcomputer. Also provided is connector 120 for connection of the insole sensor.

The user interface consists of pushbuttons 60 and 70 and alphanumeric display 80. The pushbuttons are used to initiate data collection, initiate data analysis and display, initiate offloading of data, and reset the device. Specific function of the individual pushbuttons is communicated to the user by the alphanumeric display. In this embodiment the user has the option of tailoring the analysis of ground contact times and daily activity to his or her unique situation by inputting through the display 80 and user buttons 60 and 70 gender (M or F), age, height, and body weight.

Figure 9:
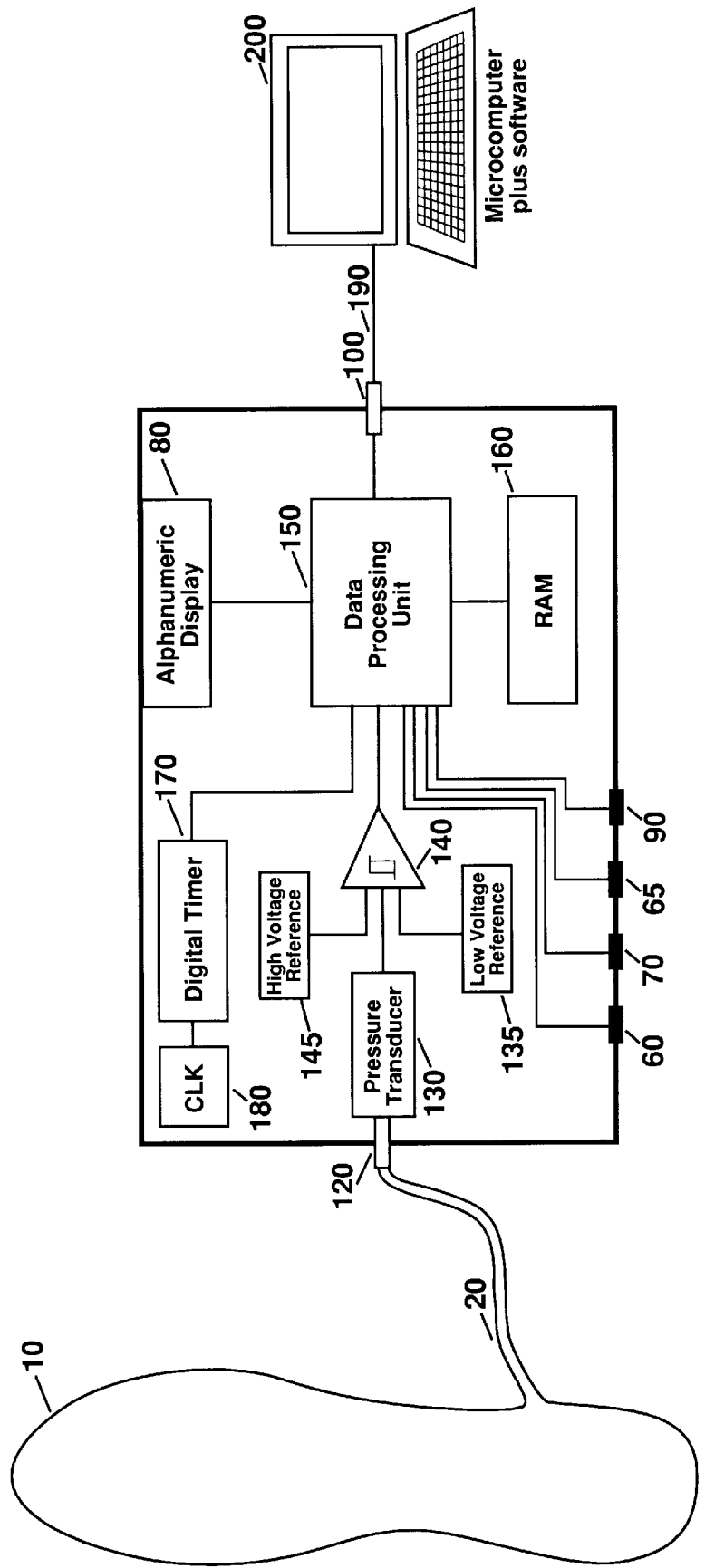
FIG. 9 is a block diagram of the internal components of the data processing/logging unit.

FIG. 9 is a block representation of the data processing/logging unit. Compression of the insole 10 during foot-ground contact results in an internal gas pressure increase which is detected by transducer 130. Any small pressure transducer is suitable in this application, such as the Motorola MPX5100. Output of the transducer is connected to the signal input of a dual-reference Schmitt-triggered comparator 140 (such as Harris Semiconductor CA3098), the reference inputs of which are connected to two reference voltage sources 135 and 145, which are fixed at levels equivalent to the output of the transducer 130 when respectively 10% and 20% of the subject's body weight is applied to the insole 10. The data processing unit 150, which consists of a microprocessor and non-volatile (read-only) program memory detects changes in the output state of the comparator. Any change in the state triggers the data processing unit to read the current value in the 24-bit digital timer 170, which is driven by clock circuit 180 at a rate of 100 Hertz. The value is stored in the random access memory (RAM) 160. All system functions are determined by a program stored in the system's read-only memory. For advanced analysis, the contents of RAM 160 can be transferred from the data processing unit 150 through the data port 100 to the serial communication port of an external microcomputer 200 via cable 190.

Figure 10:
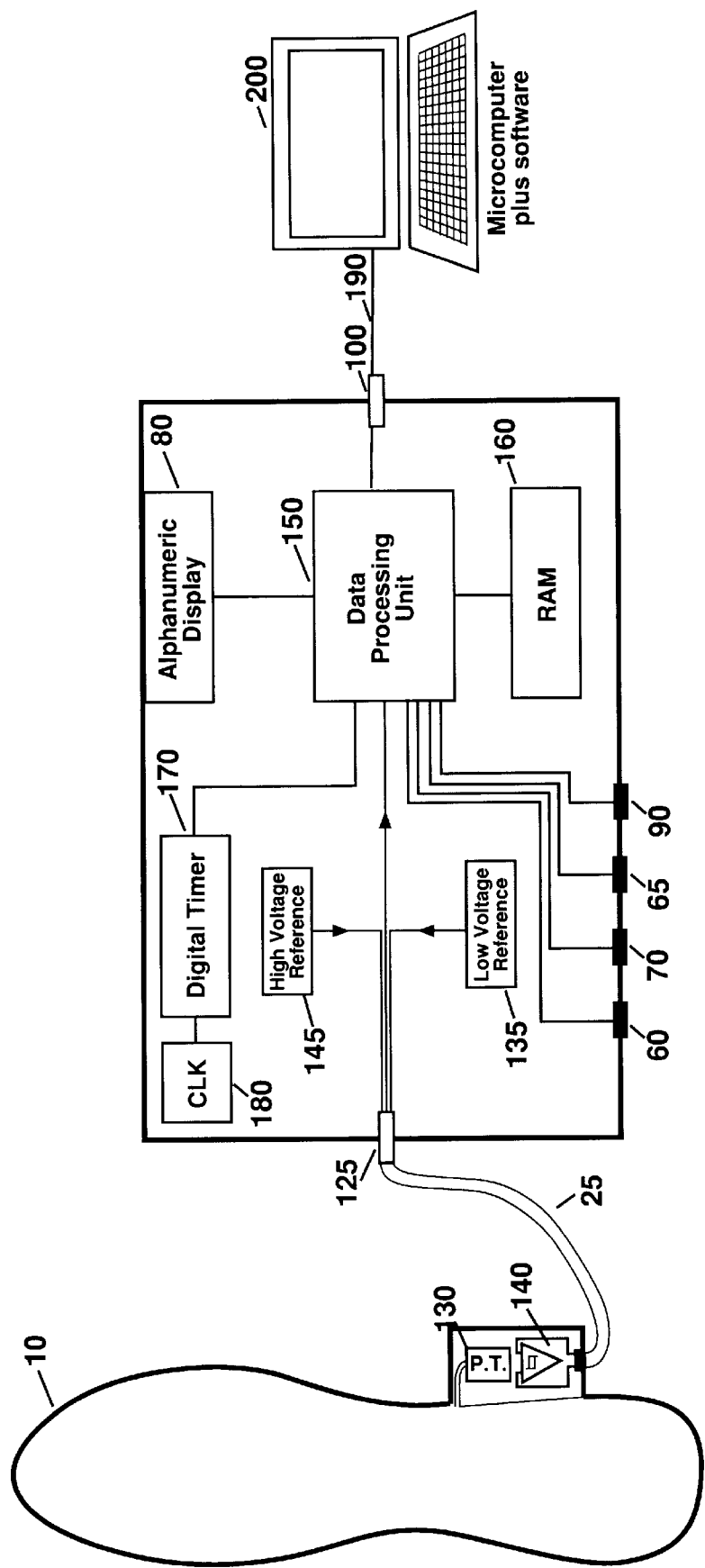
FIG. 10 is a block diagram depicting an alternative embodiment of the invention, in which some electronic components are incorporated into the insole sensor.

In an alternative embodiment of the invention, shown in FIG. 10, the pressure transducer 130 and comparator 140 are incorporated into the insole 10, which is connected to the data processing unit 150 and voltage references 135 and 145 housed in the data logging unit 90 by electrical cable 25, connected to the unit at cable connector 125.

On system reset, the microprocessor's internal address pointer is set to the beginning of the starting address of RAM, and the system waits for the first foot-down event such that the first time stored is that of a foot-down event. Consequently, the data in memory will consist of a predictable sequence of event times. Referring to the first datum as #0, all even-numbered data will be foot-down times; all odd-numbered data, foot-up times.

B. Filtering of Non-Gait-Related Foot-Ground Contact Events

Ground contact times significantly greater than those measured for slow walking (~900 ms) may likely indicate standing or sitting in one place. Because of the long duration and estimated low peak cyclic GRFz of, at most, approximately 1.0 BW, these cycles do not represent either significant errors or contributors to quantification of daily activity based on our method of a daily loading stimulus (equation 4) computed from the daily history of peak cyclic GRFzs. We have arbitrarily selected 60 seconds as a cut-off of acceptable ground contact times, i.e., longer contact times are rejected as significant timing events. As the state of our knowledge improves with more data, we may be able to optimize the selection of the upper limit.

Contact events of duration greater than approximately 900 ms ($1/t_c$=1.11 s$^{-1}$) and less than 60 seconds are unlikely to occur during walking. They may represent very slow strolling or slow shifting of weight on and off the instrumented foot. In either case, these are considered loading cycles and assigned a magnitude of one body weight. Contact events of duration less than approximately 150 ms ($1/t_c$=6.67 s$^{-1}$) corresponding to running at a speed of approximately 8 ms$^{-1}$ are not likely to occur during gait, and will be discarded as spurious. Depending on the sensitivity of our screening algorithm described below, we may be able to extend the lower limit to include extremely fast running to a minimum practical lower limit of 125 ms, equivalent to ~10 ms.$^{-1}$.

Figure 4:
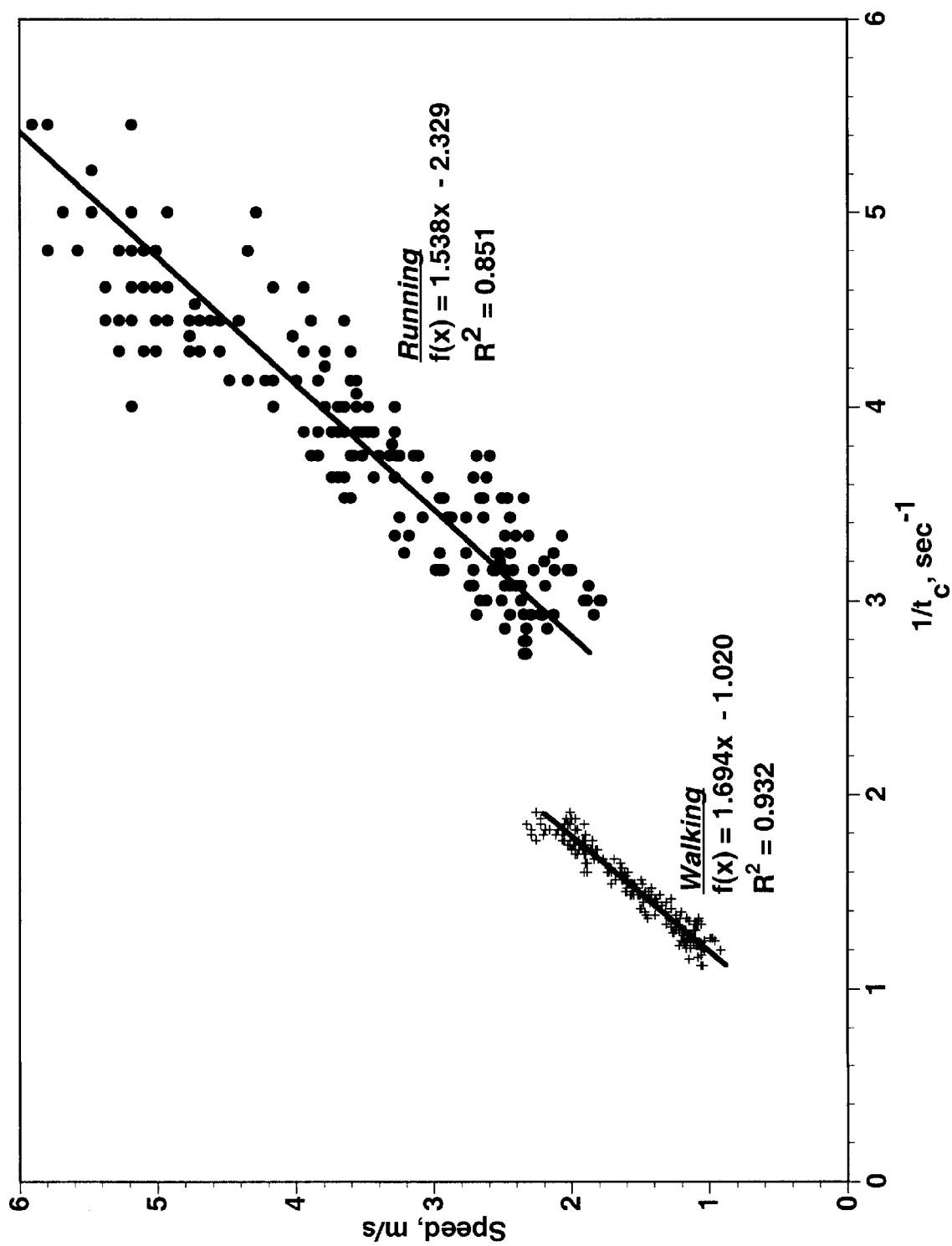
FIG. 4 is a graph showing the relationship between the reciprocal of the ground contact time and walking and running speed.

Although switch debouncing will eliminate many spurious contact events, some non-gait-related ground contact times are anticipated to occur that lie within the range of walking and running. From FIGS. 2a and 4 it is clear that walking contact times do not overlap running contact times (0.50 s<$t_{c,walking}$<0.90 s; 0.15 s<$t_{c,running}$<0.37 s ). However, during logging of daily activity over long periods with our insole force sensor, we have detected gait-related contact times in the contact-time zone between walking and running (0.37≦$t_{c,special\ events}$≦0.50). We have labeled these "special events" to distinguish them from well-defined activities. We attribute most of these to non-steady state locomotion such as transitioning to and from jogging, ascending and descending stairs, and jumping. In this embodiment these contact times will be treated as if they were walking cycles for all calculations. Thus "walking" will span the interval (0.39 s<$t_{c,walking}$<0.90 s) and running (0.15 s<$t_{c,running}$≦0.39 s). The transition point (0.39 s) is chosen as the intersection of the GRFz/(1/$t_c$) regressions lines for walking and running (equations 8 and 9, FIG. 2a).

Figure 5:
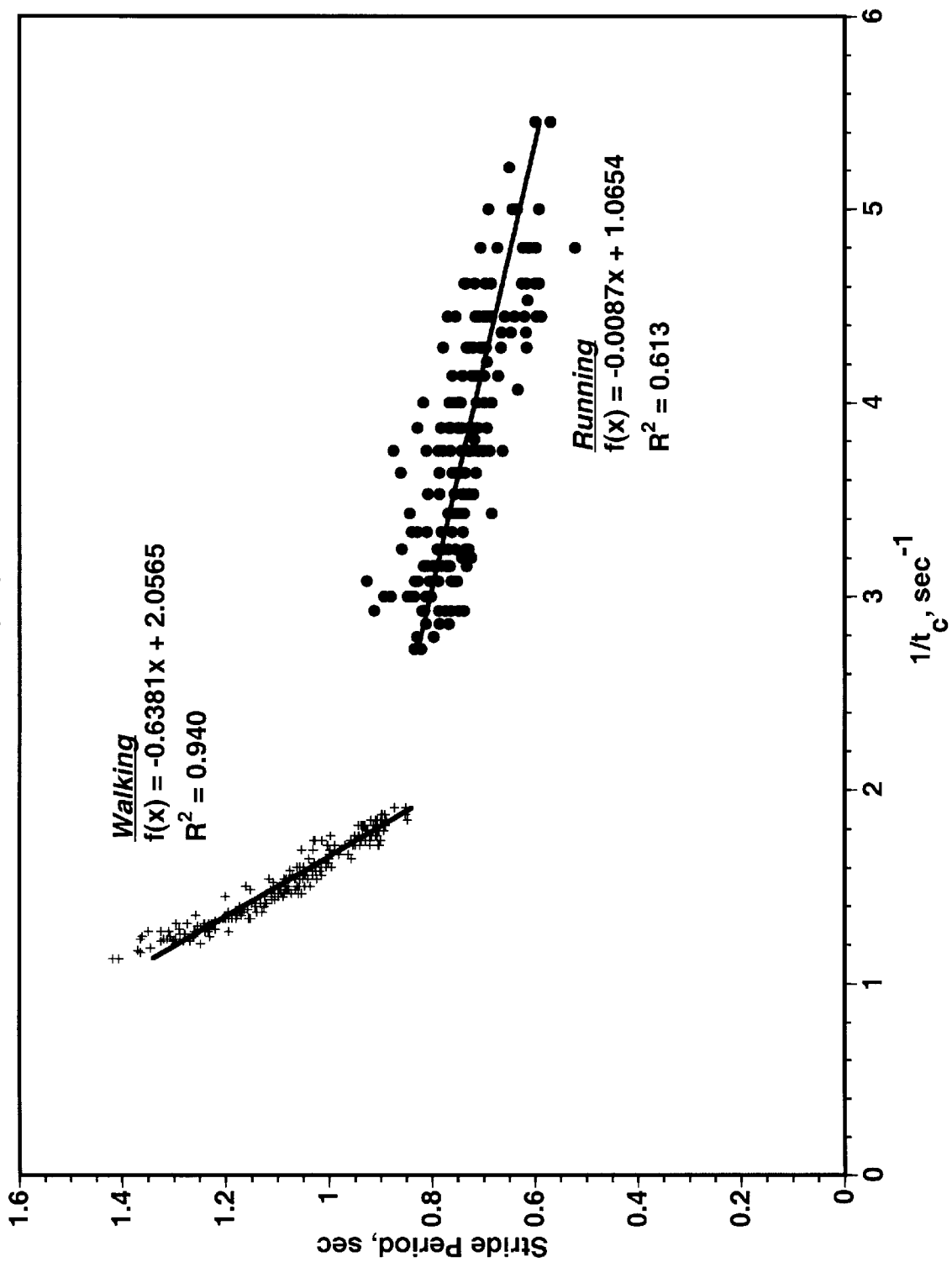
FIG. 5 is a graph showing the relationship between the reciprocal of the ground contact time and stride period during walking and running.

Cycles classified as walking or running on the basis of $t_c$ are further verified by analysis of the stride period (T), the interval between successive cycles. During steady-state gait, there exists a strong correlation between T and $t_c$ (FIG. 5), such that a cycle possessing a particular $t_c$ will occur at a predictable time interval from the subsequent cycle. The screening algorithm first determines from the value of the contact time whether the cycle is potentially a "walking", i.e., a true walking cycle or a "special event", or a running cycle.

Depending on the identification of the cycle as either walking or running, the appropriate regression equation (see FIG. 5) relating stride period to the reciprocal of contact time is used to determine the "expected" stride period for the ground contact time in question. If the actual stride period, measured as the difference in time between successive foot-down events, is outside of the expected value and its 95% confidence interval, then the ground contact-time event (foot-down and foot-up) is discarded. With more experience we may wish to adjust the limits on the confidence interval. Following this processing, the remaining ground contact events are considered to represent true walking (and special events) and running gait cycles.

C. Data Processing and Analysis c.1: Contact Times, Stride Periods, Peak Cyclic GRFzs Data are analyzed by the onboard microprocessor, or the contents of RAM are offloaded to a host computer for analysis. From the train of remaining event times, a step-by-step record of contact times and stride periods is generated by subtracting even-odd pairs and even-even (or odd-odd) pairs, respectively. From the history of contact times, a history of cyclic loading events (cycle magnitudes) is generated based on empirically-determined regression equations from a large pool of human subjects.

Regression equations were generated from data collected on 24 subjects. Equations (8) and (10) are used to compute peak cyclic GRFz from contact times and contact times normalized by stride period for walking and running, respectively. The regression equations are considered good approximations to regressions equations obtained over a broad range of subjects representative of the population. As more data become available, these may be adapted.

c.1: Gait Variables

During analysis, cycle counts and sums of 1/$t_c$ and T are maintained separately for all cycles positively identified as steady-state walking and running as described previously. For running, a sum of T/$t_c$ is maintained as well. At the end of analysis, separate average values of 1/$t_c$ are calculated for walking and running by division of the respective 1/$t_c$ sums by the respective cycle counts. Based on the separate empirical relationships between walking and running speed and 1/$t_c$ (FIG. 4), these average values are converted to representative steady-state gait speeds for walking and running. Separate sums of T for walking and running provide a measure of total time spent performing each type of gait. Separate cycle counts provide a measure of total walking steps and total running steps.

c.2: Total Gait-Related Energy Expenditure

Total Gait-related energy expenditure is determined as the sum of walking-specific and running-specific energy expenditures. Because of the fundamental differences in the underlying mechanics of these two types of gait, the respective values for energy consumption are calculated separately. For walking, the rate of energy expenditure has been reported as a function of gait speed and gross body weight by Passmore and Durnin, 1955. The user's average energy consumption rate during walking is determined in terms of his average walking speed (as described above) and body mass by bilinear interpolation of the empirical data. Total walking-specific energy expenditure is calculated as the product of average energy rate and total walking time. Running-specific energy expenditure is calculated in terms of instantaneous rates of energy expenditure based on the model of Kram and Taylor, 1990. Across a wide range of species, they found the rate of energy consumption E to be well approximated as:

$$\dot{E} = \frac{W \cdot c}{t_c} \tag{11}$$

where W is the body weight and c is a constant found empirically equal to 0.183 J/N. It follows that the per-step energy consumption $E_{step}$ can be described as:

$$E_{step} = W \cdot c \cdot \frac{T}{t_c} \tag{12}$$

Total running-specific energy consumption can be estimated as the sum of all per-step values, or:

$$E_{running} = W \cdot c \cdot \sum \frac{T}{t_c} \tag{13}$$

c.3: Skeletal Loading: Activity Index, Bone Density Index, "Equivalent Age"

Figure 11:
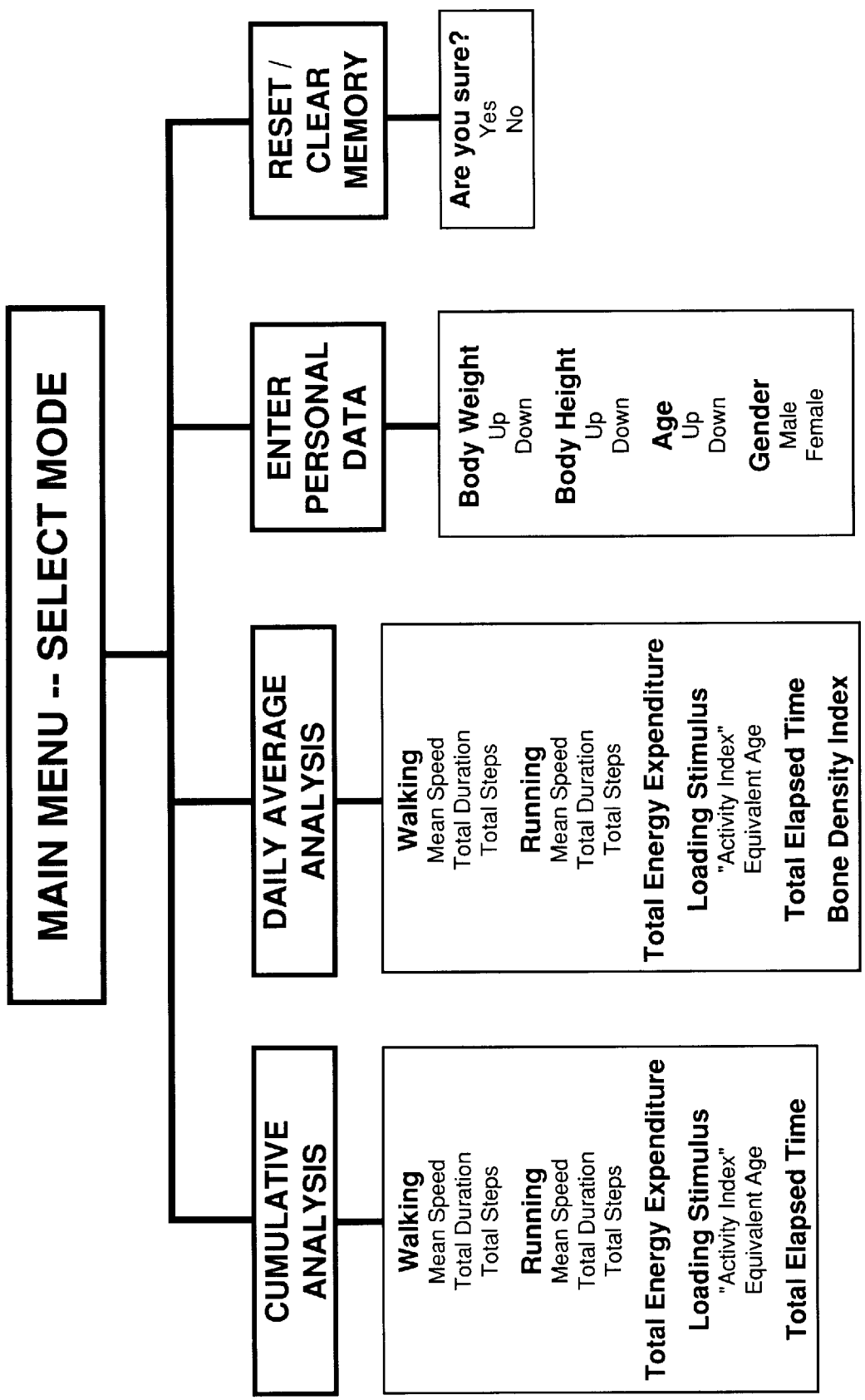
FIG. 11 is a flow chart summarizing the user menu structure.

The Activity Index (AI) and Bone Density Index (BDI) are computed from equations (6) and (7). Currently the best estimate for the value of m is 4.0, but there is some indication it may be higher or even bi-linear. Thus the value currently chosen is the best estimate, but may change according to future research. FIG. 11 shows how these are accessed by the user.

Once a data base is collected of daily peak GRFz loading histories among the population as a function of age, it will be possible to provide the user with an indication of his/her activity status with respect to the general population. The user's loading history can be summarized as an "equivalent age" based upon a comparison of his or her Activity Index with population data contained internally.

The "equivalent age" is the same as the user's age if the intensity of the user's loading history is average for his age; less than the user's age if he is more active than average for his age; greater than the user's age if he is less active than average for his age. Following internal data analysis, the "equivalent age" is communicated to the user by the alphanumeric display.

c.4: Offline Analysis

The system is designed to be self-contained, performing data collection and analysis and display within the portable unit Users desiring more detailed data presentation and analysis, as well as long-term data logging capabilities, can interface the unit to an external microcomputer 200 with graphical display capabilities for further offline analysis. Special software to handle data transfer, analysis, and display is initiated on the microcomputer. The user connects the unit's data port 100 to the microcomputer's serial communication port using data cable 190. Using the pushbuttons 60, 65 and 70, the user initiates the data transfer. The contents of RAM are transferred to the microcomputer. The software recalculates force cycles from the contact time history, using user-specific regression relationships if available. Peak vertical (GRFz), peak medial, lateral, anterior, and posterior GRF, peak and average vertical (GRFz-rate), medial-lateral, and anterior-posterior loading rates (dGRF/dt) are similarly calculated for each contact event, using empirically-determined regression relationships (derived, but not listed here).

The microcomputer software provides the user with a number of advanced analyses of the loading history: 1) 2-D histogram of all significant loading cycles (z-axis) organized according to cycle range, i.e., magnitude (x-axis) and cycle offset (y-axis); 2) 1-D histogram of all significant loading cycles projected onto the cycle range (x-axis) with fitted Weibull distribution; 3) 1-D histogram of peak loading and unloading rates; 4) 1-D histogram of cumulative damage density for estimation of bone remodeling stimulus; 5) comparison of current data to that stored from previous collection sessions.

What is claimed is:

1. An apparatus for determining peak vertical ground reaction forces, comprising:

a) an instrumented insole inserted into a user's shoe, b) a data collection means for measuring foot to ground contact time, c) a data processing means for processing said ground contact time data, and d) a calculating means for indirectly estimating peak vertical reaction forces using processed ground contact time data.

2. An apparatus for determining a user's daily activity from a determination of peak vertical ground reaction forces, comprising:

a) an instrumented insole inserted into a user's shoe, b) a data collection means for measuring foot to ground contact time, c) a data processing means for processing said contact time data, and d) a calculating means for calculating peak vertical ground reaction forces and calculating a daily Activity Index, AI, and Bone Density Index, BDI as:

$$AI \equiv \left[\sum (GRF_{zi})^m\right]^{\frac{1}{m}} \text{ and } BDI \equiv \beta^{\frac{1}{2}}\left[\sum (GRF_{zi})^m\right]^{\frac{1}{2m}}.$$

* * * * *